United States Patent [19]

Irikura

[11] 4,146,719

[45] Mar. 27, 1979

[54] PIPERAZINYL DERIVATIVES OF QUINOLINE CARBOXYLIC ACIDS

[75] Inventor: Tsutomu Irikura, Tokyo, Japan

[73] Assignee: Kyorin Seiyaku Kabushiki Kaisha, Tokyo, Japan

[21] Appl. No.: 878,600

[22] Filed: Feb. 16, 1978

[30] Foreign Application Priority Data

May 16, 1977 [JP] Japan .................................. 52/56219

[51] Int. Cl.$^2$ ............................................ C07D 295/00
[52] U.S. Cl. ...................................... 544/363; 424/250
[58] Field of Search .......................................... 544/363

[56] References Cited

U.S. PATENT DOCUMENTS 4,017,622  4/1977  Minami et al. ........................ 544/363

FOREIGN PATENT DOCUMENTS 2341146  2/1974  Fed. Rep. of Germany.
2362553  6/1974  Fed. Rep. of Germany.

Primary Examiner—Paul M. Coughlan, Jr.
Attorney, Agent, or Firm—Toren, McGeady and Stanger

[57] ABSTRACT

This invention relates to new compounds of value as antibacterial agent. More particularly, it relates to piperazinyl derivatives of quinoline carboxylic acids, the hydrates, and the acid addition salts thereof.

4 Claims, 3 Drawing Figures

Ratio of serum concentration to M.I.C. on Escherichia coli ATCC 10536

—o— Compound (II)
—▲— Nalidixic acid
—●— Pipemidic acid

PIPERAZINYL DERIVATIVES OF QUINOLINE CARBOXYLIC ACIDS

DETAILED DESCRIPTION OF THE INVENTION

Figure 1:
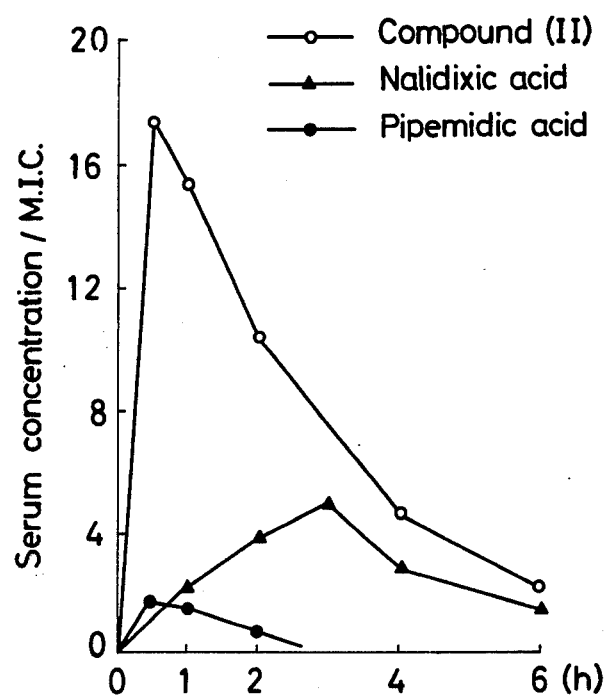

Antibacterial agent such as nalidixic acid has been proved highly effective in the therapy of infections due to gram-negative bacteria, but such agent suffers from the serious drawback of being ineffective against numerous strains of bacteria, e.g., most gram-positive bacteria and Pseudomonas aeruginosa, of which infection has progressively increased for the last two decades and is one of the infections which are extremely refractory to chemotherapy. The compounds of the present invention are particularly useful in that they possess potent antibacterial activity against both gram-positive and gram-negative bacteria, including Pseudomonas aeruginosa.

The new compounds of the present invention are quinoline carboxylic acid derivative having the formula;

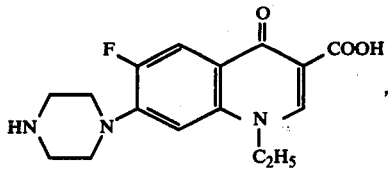

the hydrates and the acid addition salts thereof, such as the hydrochloride.

The products of the present invention are prepared by heating piperazine with an acid having the formula;

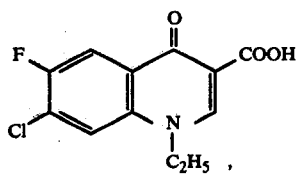

in a non-reactive solvent such as, for example, water, alcohol, pyridine, picoline, N,N-dimethylformamide, dimethylsulfoxide, hexamethylphosphoric triamide, or the like, or in the absence of a solvent, at a temperature between about room temperature and about 200° C., preferably between about 100° and 180° C.

The following examples serve to illustrate the invention.

EXAMPLE 1

Preparation of 1-ethyl-6-fluoro-1,4-dihydro-7-(1-piperazinyl)-4-oxoquinoline-3-carboxylic acid pentahydrate (I)

A mixture of 1-ethyl-6-fluoro-7-chloro-1,4-dihydro-4-oxoquinoline-3-carboxylic acid (1.9g), piperazine hexahydrate (15g) and water (15 ml) was heated at 170° C. in a sealed tube for 16 hr. After evaporation of the solvent, the residue was acidified with diluted hydrochloric acid, heated at 100° C., and the hot solution was filtered. The filtrate was evaporated to dryness. The residue was dissolved in 10% sodium hydroxide and neutralized with acetic acid. The precipitate was collected, washed with water, dried, and recrystallized from ethanol to give 1-ethyl-6-fluoro-1,4-dihydro-7-(1-piperazinyl)-4-oxoquinoline-3-carboxylic acid pentahydrate (I) as colorless powder, m.p.: 226°–227° C. Mass spectrum m/e: 319 ($M^+$).

EXAMPLE 2

Preparation of 1-ethyl-6-fluoro-1,4-dihydro-7-(1-piperazinyl)-4-oxoquinoline-3-carboxylic acid (II)

The compound (I) was dried at 100°–200° C. in vacuo to give 1-ethyl-6-fluoro-1,4-dihydro-7-(1-piperazinyl)-4-oxoquinoline-3-carboxylic acid (II) as colorless powder, m.p.: 215°–220° C. Mass spectrum m/e: 319 ($M^+$), 275 ($M^+$-$CO_2$).

EXAMPLE 3

Preparation of 1-ethyl-6-fluoro-1,4-dihydro-7-(1-piperazinyl)-4-oxoquinoline-3-carboxylic acid hydrochloride (III)

The compound (I) or (II) was dissolved in ethanol and acidified with concentrated hydrochloric acid. The resulting precipitate was collected, washed with ethanol, and dried to give 1-ethyl-6-fluoro-1,4-dihydro-7-(1-piperazinyl)-4-oxoquinoline-3-carboxylic acid hydrochloride (III) as colorless needles, m.p. above 300° C.

|  | C | H | N |
|---|---|---|---|
| Anal. Calcd. for $C_{16}H_{19}O_3N_3ClF$ | 54.01 | 5.38 | 11.81 |
| Found: | 53.85 | 5.43 | 11.62 |

EXAMPLE 4

Preparation of 1-ethyl-6-fluoro-1,4-dihydro-7-(1-piperazinyl)-4-oxoquinoline-3-carboxylic acid (II) and the hydrate (I)

A mixture of 1-ethyl-6-fluoro-7-chloro-1,4-dihydro-4-oxoquinoline-3-carboxylic acid (22g) and piperazine hexahydrate (160g) was heated at 135°–145° C. in an autoclave for 18.5 hr. The mixture was evaporated to dryness and dissolved in 10% sodium hydroxide. The solution was neutralized with acetic acid. The precipitate was collected, washed with water, dissolved in 30% acetic acid, and filtered. The filtrate was neutralized with 10% sodium hydroxide. The resulting precipitate was collected, washed with water and ethanol, and dried at 140°–145° C. in vacuo for 1.5 hr. to give 14g (54%) of 1-ethyl-6-fluoro-1,4-dihydro-7-(1-piperazinyl)-4-oxoquinoline-3-carboxylic acid (II) as colorless powder, m.p. 227°–228° C.

|  | C | H | N |
|---|---|---|---|
| Anal. Calcd. for $C_{16}H_{18}O_3N_3F$: | 60.18 | 5.68 | 13.16 |
| Found: | 60.31 | 5.70 | 13.24 |

The compound (II) was dissolved in 10% sodium hydroxide and neutralized with acetic acid. The precipitate was washed with water and dried at room temperature to afford 1-ethyl-6-fluoro-1,4-dihydro-7-(1-piperazinyl)-4-oxoquinoline-3-carboxylic acid hydrate (I) as colorless powder, m.p.: 226°–227° C.

|  | C | H | N |
|---|---|---|---|
| Anal. Calcd. for $C_{16}H_{18}O_3N_3F \cdot 5H_2O$: | 46.94 | 6.89 | 10.26 |

-continued

|        | C     | H    | N     |
|--------|-------|------|-------|
| Found: | 47.34 | 6.68 | 10.30 |

EXAMPLE 5

Preparation of 1-ethyl-6-fluoro-1,4-dihydro-7-(1-piperazinyl)-4-oxoquinoline-3-carboxylic acid (II)

A mixture of 1-ethyl-6-fluoro-1,4-dihydro-7-(1-piperazinyl)-4-oxoquinoline-3-carboxylic acid (0.45g), piperazine (0.73g), and β-picoline (4 ml) was heated at 140°–145° C. for 8 hr. The reaction mixture was treated in the same way as described in EXAMPLE 4 to give 0.34g (64%) of 1-ethyl-6-fluoro-1,4-dihydro-7-(1-piperazinyl)-4-oxoquinoline-3-carboxylic acid (II) as colorless powder, m.p.: 224°–226° C.

It is known that most of drugs such as Quinoform and Ethambutol which form chelates with metal ions in vivo produce undesirable side effects. It was reported that nalidixic acid afforded chelate compound when treated with ferric ion (Chem. Abstr., 62, 15600h (1965)). When nalidixic acid was mixed with one third molar equivalent of ferric chloride hexahydrate in the presence of a molar equivalent of sodium hydroxide in water, the absorption maxima at 256 and 326 nm of nalidixic acid shifted to shorter wave length at 248 and 311 nm, respectively, and 3:1 chelate compound of nalidixic acid and ferric ion was obtained.

On the other hand, the compound (II) of the present invention did not give any chelate compound when treated with ferric ion under the above condition.

Usefulness of the compounds of the present invention as antibacterial agent has been demonstrated by the following experiments.

Experiment 1

Antibacterial activity (in vitro)

The minimum inhibitory conceptration (M.I.C.) of the compound (II) was assayed by the agar dilution streak method against four strains of *Pseudomonas aeruginosa* and other pathogenic bacteria. As shown in Table 1, nalidixic acid and pipemidic acid exerted antibacterial activity mainly on gram-negative bacteria and were inactive on many strains of gram-positive bacteria and many *Pseudomonas aeruginosa* strains, those are gram-negative. On the other hand, the compound (II) was more active than nalidixic acid and pipemidic acid against both of gram-positive and gram-negative bacteria, and it was proved to be more active than gentamicin and carbenicillin against gram-negative bacteria including *Pseudomonas aeruginosa*.

The compound (II) showed a broad spectrum of activity against gram-positive and gram-negative bacteria, and it inhibited even such bacteria those were not susceptible to nalidixic acid, pipemidic acid and carbenicillin.

Thus, the compound (II) is promising antibacterial agent being more potent and broader antibacterial activity against pathogenic bacteria including *Pseudomonas aeruginosa* than other synthetic chemotherapeutic agents.

Table 1
Antibacterial Spectrum

| Organisms | Grams | Compound (II) | PPA | NA | GM | CBPC |
|---|---|---|---|---|---|---|
| *Bacillus subtilis* PCI 219 | + | 0.39 | 6.25 | 6.25 | 0.10 | 0.39 |
| *Staphylococcus aureus* 209P | + | 0.78 | 25 | 100 | 0.10 | 0.39 |
| *Sta. aureus* ATCC 14775 | + | 1.56 | 100 | >100 | 0.10 | 6.25 |
| *Streptococcus pyogenes* IID 692 | + | 3.13 | >100 | >100 | 6.25 | 0.10 |
| *Str. pyogenes* S-8 | + | 1.56 | >100 | >100 | 6.25 | 0.10 |
| *Str. faecalis* IID 682 | + | 3.13 | — | — | 50 | 100 |
| *Diplococcus pneumoniae* IID 552 | + | 12.5 | >100 | >100 | 12.5 | 0.39 |
| *Corynebacterium pyogenes* IID 548 | + | 3.13 | 100 | — | 0.78 | 0.20 |
| *Mycobacterium phlei* IFO 3142 | + | 0.39 | 12.5 | 100 | 6.25 | >200 |
| *My. smegmatis* IFO 3083 | + | 1.56 | 50 | >100 | 0.20 | 6.25 |
| *Escherichia coli* NIHJ | − | 0.10 | 1.56 | 3.13 | 0.39 | 1.56 |
| *E. coli* ATCC 10536 | − | 0.05 | 1.56 | 3.13 | 0.39 | 1.56 |
| *Proteus vulgaris* IFO 3167 | − | 0.05 | 3.13 | 3.13 | 0.20 | 6.25 |
| *Pr. vulgaris* XK Denken | − | 0.20 | 6.25 | 3.13 | 0.10 | 0.39 |
| *Klebsiella pneumoniae* IFO 3512 | − | 0.05 | 1.56 | 1.56 | 0.20 | >200 |
| *Salmonella enteritidis* IID 604 | − | 0.20 | 12.5 | 12.5 | 1.56 | 12.5 |
| *Shigella sonnei* IID 969 | − | 0.10 | 1.56 | 1.56 | 0.78 | 1.56 |
| *Haemophilus influenzae* IID 986 | − | 0.05 | 3.13 | 1.56 | 1.56 | 0.39 |
| *Neisseria perflava* IID 856 | − | 0.05 | 1.56 | 1.56 | 0.78 | 1.56 |
| *Pseudomonas aeruginosa* V-1 | − | 0.39 | 12.5 | 100 | 0.78 | 12.5 |
| *Ps. aeruginosa* IFO 12689 | − | 1.56 | 25 | >200 | 12.5 | 100 |
| *Ps. aeruginosa* IID 1210 | − | 1.56 | 50 | >200 | 12.5 | 100 |
| *Ps. aeruginosa* IID 1130 | − | 0.78 | 25 | >200 | 3.13 | 200 |

PPA : Pipemidic acid;
NA : Nalidixic acid;
GM : Gentamicin;
CBPC : Carbenicillin

Experiment 2

Preventive effect of the compound (II) against systemic infection with *Pseudomonas aeruginosa* in mice Systemic infection was produced by inoculating male mice (strain: ddY, 6 weeks old, body weight: 28–33g) in intraperitoneally with *Pseudomonas aeruginosa* IID 1210 suspended in 0.5 ml of Brain heart infusion broth (Eiken) containing 5% mucin. The compound (II) and pipemidic acid were suspended in 0.5% carboxymethyl cellulose solution, respectively, and carbenicillin was dissolved in water. Each of these test materials was administered to the mice twice, immediately after and then 6 hours after the inoculation, and the therapeutic effect of each compounds was judged from the survival rate. A comparison of compound efficacy was made by 50% effective dose ($ED_{50}$) calculated by probit analysis (1) and a 95% confidence limit that was calculated by the method of Litchfield and Wilcoxon (2). As shown in Table 2, the compound of EXAMPLE 2 effectively protected the mice from *Pseudomonas aeruginosa* infection, and it was confirmed that it was more potent than pipemidic acid and carbenicillin. $LD_{10}$ of the compound (II) is over 4g/kg in mice and so the compound (II) is excellent in safety zone ($LD_{10}/ED_{90}$ = over 21.6).

(1) Miller L. C. and M. L. Tainter: Estimation of the $ED_{50}$ and its error by means of logarithmic-probit graph paper Proc. Soc. Exp. Biol. Med. 57 261–264 (1944)

(2) Litchfield J. T. and F. Wilcoxon: A simplified method of evaluating dose - effect J. Pharmacol. 92 99–113 (1948)

Table 2

Preventive effect of the compound (II) against systemic infection with *Pseudomonas aeruginosa* in mice

| Compounds | Challenge dose (cells/mouse) | $ED_{50}$ (mg/kg) (95% confidence limit) | $ED_{90}$ (mg/kg) |
|---|---|---|---|
| Compound (II) | $3.5 \times 10^4$ | 98.0(79.7–120.5) | 185 |
| Pipemidic acid | $3.5 \times 10^4$ | 400(317–504) | 1120 |
| Carbenicillin | $3.5 \times 10^4$ | 800(630–1,016) | 1430 |

Compound (II) and Pipemidic acid were administered orally, Carbenicillin was administered subcutaneously.

Experiment 3

Preventive effect of the compound (II) against ascending kidney infection in mice with *Escherichia coli*

Ascending kidney infection was induced in female mice (strain: ddY, 6 weeks old, body weight: 22–26g), by instilling *Escherlichia coli* NIHJ JC-2 suspended in 0.04 ml of Tryptosoya broth (Nissan) into the urinary tract of mice anesthetized with sodium pentobarbital and by holding for 6 hours the mice in plastic tubes (diameter 25 mm) and clamping the outlet of urinary tract.

The compound (II), nalidixic acid and pipemidic acid were suspended in 0.5% carboxy methyl cellulose solution, respectively. Each of these test material was orally administered 3 hours after inoculation. Mice were sacrificed 48 hours after inoculation. Kidneys were removed aseptically and bisected, and the two halves were pressed and streaked on agar plate containing Desoxycholate medium (Nissan). The therapeutic effect of each compound was evaluated from the absence of growth on the agar surface after 20 hours of incubation at 37° C. A comparison of compound efficacy was made by 50% effective dose ($ED_{50}$) calculated by probit analysis and a 95% confidence limit that was calculated by the method of Litchfield and Wilcoxon.

As shown in Table 3, the compound of EXAMPLE 2 was effective against ascending kidney infection with *Escherichia coli* in mice and it was confirmed that the compound (II) was more potent than nalidixic acid and pipemidic acid.

$LD_{10}$ of the compound (II) is over 4 g/kg in mice and the compound (II) is excellent in safety zone ($LD_{10}/ED_{90}$ = over 65.6).

Table 3

Preventive effect of the compound (II) against ascending kidney infection with *Escherichia coli* in mice

| Compounds | Challenge dose (cells/mouse) | $ED_{50}$ (mg/kg) (95% confidence limit) | $ED_{90}$ (mg/kg) |
|---|---|---|---|
| Compound (II) | $3.2 \times 10^7$ | 15.0 (8.6 – 26.3) | 61 |
| Nalidixic acid | $3.2 \times 10^7$ | 86.0 (45.3 – 163) | 345 |
| Pipemidic acid | $3.2 \times 10^7$ | 74.0 (51.0 – 107) | 235 |

Experiment 4

Concentrations of the compound (II) in serum after a single oral administration of 50 mg/kg in rats Concentrations of the compound (II) in serum were determined by microbiological assay. Nutrient agar was heated and melted. *Escherichia coli* NIHJ JC-2 was added to melted agar, and well mixed, and 5 ml of the mixture was placed in Petri dish. Penicylinders were placed on the solidified agar, and the cylinder was filled with serum sample. The plate was placed in the incubator of 37° C. for 20 hours. The diameter of the inhibition zone was measured. The serum was sampled at 0.5, 1, 2, 4, and 6 hours after giving the compound (II) in rat.

The serum concentrations of compound (II) after a single oral administration of 50 mg/kg were shown in Table 4. Absorption of the compound (II) was rapid, and the concentration peak was at 30 min. after oral administration. The antibacterial activity of the compound (II) was not decreased by serum.

Table 4

Serum concentration of compound (II) after a single oral administration of 50 mg/kg in rat

| Time after administration | Concentration µg/ml |
|---|---|
| 0.5 | 0.87 ± 0.11 |
| 1 | 0.77 ± 0.13 |
| 2 | 0.52 ± 0.10 |
| 4 | 0.23 ± 0.02 |
| 6 | 0.11 ± 0.01 |

Experiment 5

Concentrations of compound (II) in serum at 30 min. after a single oral administration in rats The concentrations of compound (II) in serum of rats at 30 minutes after a single oral administration were shown in Table 5. The concentrations of compound (II) in serum were assayed by the microbiological method described in the experiment 4.

The antibacterial activity of the compound (II) was not decreased by serum. Serum concentration of the compound depended on the dose from 25 mg/kg to 400 mg/kg.

Table 5

Concentration of compound (II) in serum at 30 min. after a single oral administration in rats

| Dose (mg/kg) | Concentration (µg/ml) mean ± S.E. |
|---|---|
| 25 | 0.31 ± 0.04 |
| 50 | 0.87 ± 0.11 |
| 100 | 1.42 ± 0.23 |
| 200 | 2.23 ± 0.30 |
| 400 | 3.37 ± 0.35 |

Experiment 6

Figure 2:
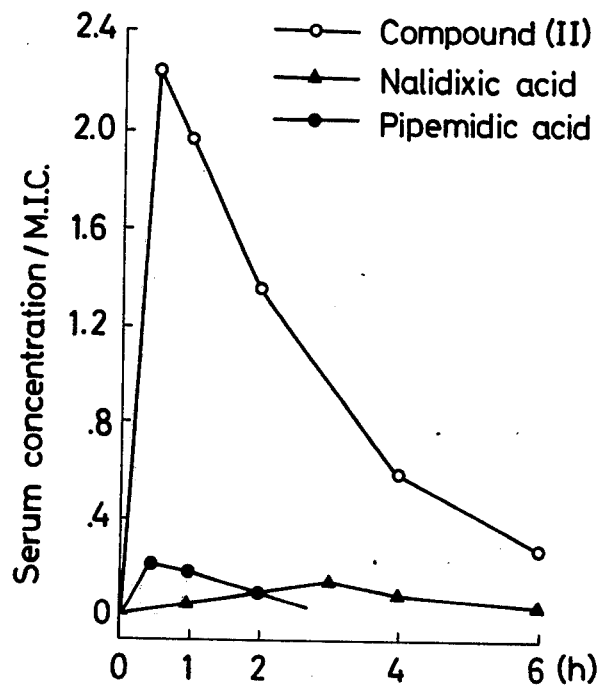
Figure 3:
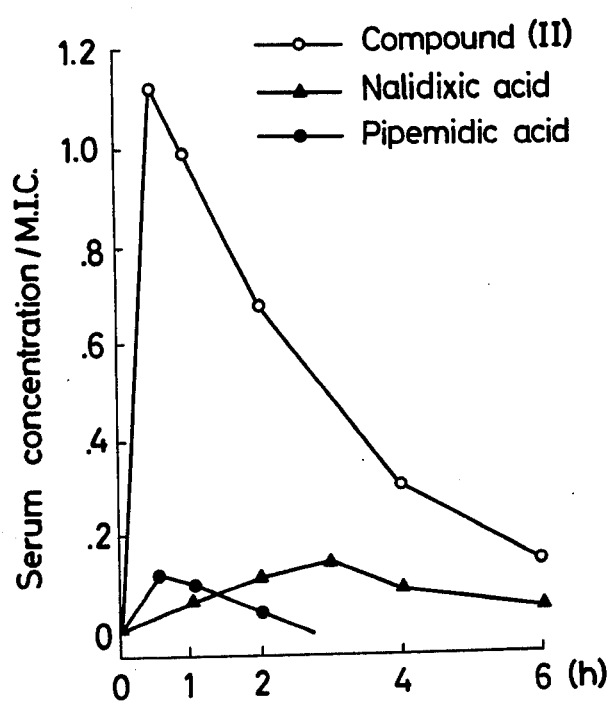

The concentration ratio of the compound (II) in serum to minimum inhibitory concentration (M.I.C.) on pathogenic bacteria after oral administration of 50 mg/kg in rats The concentration ratios of compound (II), nalidixic acid and pipemidic acid in serum of rats to M.I.C. on pathogenic bacteria were shown in FIGS. 1–3, respectively.

As shown in FIGS. 1–3, the absorption of the compound (II) was rapid, and the serum concentrations were 18 times of M.I.C. on *Escherichia coli* at 30 minutes and 2 times at 6 hours after oral administration. On the other hand, the concentration ratios of halidixic acid and pipemidic acid were smaller than that of the compound (II) and serum levels of pipemidic acid were maintained till only 2 hours after oral administration.

The compound (II) could be expected to take more effect than nalidixic acid and pipemidic acid against infections of the preceding bacteria. In addition, the compound (II) could be expected to take more effect than those of nalidixic acid and pipemidic acid against infections of *Pseudomonas aeruginosa* and gram-positive bacteria.

Experiment 7

Concentrations of compound (II) in tissues after a single oral administration of 50 mg/kg in rats Concentrations of compound (II) in tissues were assayed by the microbiological method described in the experiment 4 except using tissue homogenate instead of serum. The tissue homogenates were prepared with 1:4 homogenates in M/15 phosphate buffer (pH 7.5). Free concentration was calculated from standard curve of the compound (II) in M/15 phosphate buffer. Total concentration was calculated from standard curve of the compound (II) in tissue homogenate. The tissue concentrations of compound (II) after a single oral administration of 50 mg/kg were shown in Tables 6 and 7.

Antibacterial activity of the compound (II) was decreased by liver and kidney homogenate.

Table 6

Concentration of compound (II) in tissues after a single oral administration of 50 mg/kg in rats

| (Free concentration) | Tissue level (μg/g) | | | | |
|---|---|---|---|---|---|
| | 0.5 | 1 | 2 | 4 | 6 (hrs.) |
| Liver | 4.1±0.9 | 3.7±0.6 | 2.5±0.5 | 1.2±0.2 | 0.7±0.1 |
| Kidney | 7.4±1.4 | 6.8±1.2 | 4.4±0.6 | 1.9±0.2 | 1.0±0.1 | mean ± S.E.

| (Total concentration) | Tissue level (μg/g) | | | | |
|---|---|---|---|---|---|
| | 0.5 | 1 | 2 | 4 | 6 (hrs.) |
| Liver | 9.0±1.9 | 7.9±1.2 | 5.4±1.0 | 2.6±0.4 | 1.5±0.2 |
| Kidney | 11.1±2.1 | 10.3±2.0 | 6.5±0.9 | 3.5±0.9 | 1.4±0.1 | mean ± S.E.

Experiment 8

Tissue levels of $^{14}C$-labeled compound (II) in rats after oral administration Distribution of compound (II) was studied in rats orally given a single dose of 50 mg $^{14}C$-compound (II)/kg. Tissue levels of compound (II) at 30 minutes after administration were shown in Table 8.

Table 8

Tissue levels of $^{14}C$-compound (II) in rats after oral administration (50 mg $^{14}C$-compound/kg)

| Tissue | 30 min. after administration | |
|---|---|---|
| Blood | 1.41±0.44 | μgEq/ml |
| Lung | 1.91±0.48 | μgEq/g |
| Liver | 11.09±4.78 | " |
| Kidney | 11.42±2.40 | " |
| Bladder | 15.0±20.28 | " |
| Bone | 0.73±0.28 | " |

Experiment 9

Billiary excretion in rats after a single oral administration of 50 mg/kg of the compound (II)

The concentrations of compound (II) in bile of rats after a single oral administration of 50 mg/kg were shown in Table 9, and the cumulative recovery was shown in Table 10. The compound (II), nalidixic acid and pipemidic acid concentrations in bile were assayed by the microbiological method described in the experiment 4.

The biliary levels and cumulative excretion of compound (II) were more excellent than those of nalidixic acid and pipemidic acid. The antibacterial activity of the compound (II), nalidixic acid and pipemidic acid was not influenced by bile of rats.

Table 9

The concentrations of compound (II) in bile after a single oral administration of 50 mg/kg in rats

| Time after administration (hrs.) | Biliary level (μg/ml) mean±S.E. | | |
|---|---|---|---|
| | Compound (II) | Nalidixic acid | Pipemidic acid |
| 0–3 | 31.0±3.5 | 14.7±1.5 | 27.4±2.6 |
| 3–6 | 26.4±3.2 | 16.6±2.4 | 22.6±1.7 |
| 6–24 | 18.9±1.6 | 9.3±1.6 | 10.2±1.2 |
| 24–27 | 6.7±0.9 | —* | —* |

—* Not detected (<2 μg/ml)

Table 10

The biliary excretion in rats after a single oral administration of 50 mg/kg of the compound (II)

| Time after administration (hours) | Cumulative recovery (%) mean ±S.E. | | |
|---|---|---|---|
| | Compound (II) | Nalidixic acid | Pipemidic acid |
| 0–3 | 0.60±0.06 | 0.29±0.03 | 0.60±0.07 |
| 0–6 | 1.02±0.11 | 0.56±0.05 | 1.01±0.10 |
| 0–24 | 2.43±0.23 | 1.33±0.10 | 1.97±0.09 |
| 0–27 | 2.50±0.23 | 1.33±0.10 | 1.97±0.09 |

Experiment 10

Concentrations of compound (II) in urine of rats and mice after a single oral administration As shown in Table 11, the concentrations of compound (II) in urine were assayed by the microbiological method described in the Experiment 4. The compound transferred to urine rapidly and the concentrations peak was observed at 0–6 hours.

Table 11

Concentrations of compound (II) in urine of rats and mice after a single oral administration

| Dose (mg/kg) | Time after administration (hours) | Urinary level (μg/ml) mean ±S.E. | |
|---|---|---|---|
| | | Rat | Mouse |
| 1.56 | 0–3 | 1.36±0.14 | 0.53±0.06 |
| | 3–6 | 0.93±0.14 | 0.22±0.04 |
| | 6–24 | 0.17±0.05 | 0.04±0.03 |
| | 24–27 | 0.04±0.01 | 0.03±0.02 |

Table 11-continued

Concentrations of compound (II) in urine of rats and mice after a single oral administration

| Dose (mg/kg) | Time after administration (hours) | Urinary level (μg/ml) mean ±S.E. Rat | Mouse |
|---|---|---|---|
| 3.13 | 0–3 | 3.39±0.55 | 1.76±0.19 |
|  | 3–6 | 3.78±0.44 | 1.46±0.23 |
|  | 6–24 | 0.58±0.09 | 0.27±0.04 |
|  | 24–27 | 0.03±0 | 0.14±0.01 |
| 6.25 | 0–3 | 9.69±2.30 | 3.70±0.26 |
|  | 3–6 | 8.08±1.50 | 2.04±0.13 |
|  | 6–24 | 1.36±0.20 | 3.01±0.17 |
|  | 24–27 | 0.04±0 | 0.38±0.05 |
| 12.5 | 0–3 | 21.9±3.6 | 10.3±0.9 |
|  | 3–6 | 16.8±1.6 | 8.3±0.7 |
|  | 6–24 | 4.0±0.5 | 7.4±0.8 |
|  | 24–27 | 0.06±0.02 | 1.2±0.1 |
| 25.0 | 0–3 | 56.8±11.1 | 16.2±3.3 |
|  | 3–6 | 46.4±3.8 | 20.3±1.7 |
|  | 6–24 | 13.5±3.0 | 11.7±0.9 |
|  | 24–27 | 1.2±0.5 | 2.5±0.2 |
| 50.0 | 0–3 | 89.3±19.5 | 33.1±2.8 |
|  | 3–6 | 99.2±15.9 | 27.2±3.2 |
|  | 6–24 | 32.2±0.1 | 23.1±2.0 |
|  | 24–27 | 3.1±0.9 | 7.7±1.1 |

Experiment 11

Acute toxicity

Acute toxicity of the compound (II) was examined in mice (ddY strain, 7 weeks old) and rats (Wistar strain, body weight 180–230 g). Observation period was 10 days, respectively, after a single oral, subcutaneous and intravenous administration. The $LD_{50}$ value was determined by the Litchfield-Wilcoxon method. The results were shown in Table 12.

Table 12

The $LD_{50}$ values of the compound (II)

| Animal | Route of administration | Sex | $LD_{50}$ mg/kg (95% confidence limit) |
|---|---|---|---|
| Mice | oral | male | >4,000 |
|  |  | female | >4,000 |
|  | subcutaneous | male | >1,500 |
|  |  | female | >1,500 |
|  | intravenous | male | 210 (194–227) |
|  |  | female | (207–236) |
| Rats | oral | male | >4,000 |
|  |  | female | >4,000 |
|  | subcutaneous | male | >1,500 |
|  |  | female | >1,500 |
|  | intravenous | male | 305 (288–323) |

Experiment 12

Subacute toxicity study

Subacute toxicity study of the compound (II) was carried out in rats by administering orally 250, 500 and 1000 mg/kg for 1 month. As the results, no effects of the test compound were observed in general symptom, food and water consumptions, body weight, hematological analysis, hematobiochemical analysis, the differential counts of myelocytes, biochemical analysis of liver and kidney, urinary analysis, organ weight, gross observation and histopathological findings.

Experiment 13

Effects on chromosome

The effects of the compound (II) on chromosome of myelocytes were tested by administering orally 250 and 500 mg/kg in Chinese hamster one time, and 1000 mg/kg in rats for 1 month. As the results, no effects of the test compound on chromosome of myelocytes were observed in both species.

Experiment 14

Teratogenicity study

Teratological study of the compound (II) was carried in mice by administering orally 500 and 1000 mg/kg during the period of organogenesis. As the results, teratogenic agent was not detected in the compound (II).

What is claimed is:

1. A compound having the formula

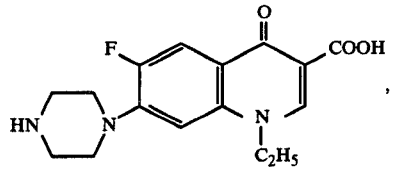

the hydrates, and the hydrochloride acid addition salts thereof.

2. 1-Ethyl-6-fluoro-1,4-dihydro-7-(1-piperazinyl)-4-oxoquinoline-3-carboxylic acid.

3. 1-Ethyl-6-fluoro-1,4-dihydro-7-(1-piperazinyl)-4-oxoquinoline-3-carboxylic acid pentahydrate.

4. 1-Ethyl-6-fluoro-1,4-dihydro-7-(1-piperazinyl)-4-oxoquinoline-3-carboxylic acid hydrochloride.

* * * * *

UNITED STATES PATENT AND TRADEMARK OFFICE

CERTIFICATE EXTENDING PATENT TERM
UNDER 35 U.S.C. 156

Patent No.    : 4,146,719

Dated         : March 27, 1979.

Inventor(s)   : Tsutomu Irikura

Patent Owner  : Kyorin Seiyaku Kabushiki Kaisha

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this First day of October 1987.

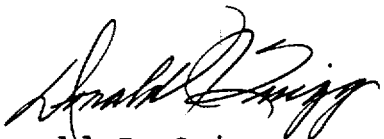

Donald J. Quigg

Assistant Secretary and Commissioner of Patents and Trademarks